United States Patent [19]

Drewes et al.

[11] Patent Number: 5,344,992

[45] Date of Patent: Sep. 6, 1994

[54] PROCESS FOR THE PREPARATION OF LINEAR 1,3-DIKETONES

[75] Inventors: Rolf Drewes, Lindenfels; Hans-Helmut Friedrich, Lautertal; Hans-Ludwig Mehner, Lampertheim; Bernd Braun, Lautertal; Walter Wecht, Rimbach, all of Fed. Rep. of Germany

[73] Assignee: Ciba-Geigy Corporation, Ardsley, N.Y.

[21] Appl. No.: 60,461

[22] Filed: May 11, 1993

Related U.S. Application Data

[63] Continuation of Ser. No. 860,297, Mar. 27, 1992, abandoned, which is a continuation of Ser. No. 690,021, Apr. 23, 1991, abandoned.

[30] Foreign Application Priority Data

Apr. 26, 1990 [CH] Switzerland .............. 1424/90-9

[51] Int. Cl.$^5$ .............................................. C07C 45/45
[52] U.S. Cl. .................................... 568/314; 568/346; 568/388; 568/42; 568/306
[58] Field of Search .............. 568/314, 346, 388, 42, 568/306

[56] References Cited

U.S. PATENT DOCUMENTS

| | | | |
|---|---|---|---|
| 3,004,932 | 10/1961 | Despléet al. | 568/314 |
| 3,362,935 | 1/1968 | Norton | 568/314 |
| 3,742,062 | 6/1973 | Chappelow et al. | 568/314 |
| 4,065,502 | 12/1977 | MacKay et al. | 568/314 |
| 4,256,657 | 3/1981 | Wheeler | 568/314 |
| 4,482,745 | 11/1984 | Maulding | 568/314 |
| 4,562,067 | 12/1985 | Hopp et al. | 568/314 |
| 5,015,777 | 5/1991 | Chisolm et al. | 568/314 |

FOREIGN PATENT DOCUMENTS

| | | |
|---|---|---|
| 1618442 | 12/1970 | Fed. Rep. of Germany ...... 568/314 |
| 1618444 | of 1971 | Fed. Rep. of Germany ...... 568/314 |

OTHER PUBLICATIONS

J. P. Anselme, Org. Syn. 32, 3716 (1967).

Derwent Abstr. WPI Acc. No. 68-19593Q/00.

Primary Examiner—James H. Reamer
Attorney, Agent, or Firm—William A. Teoli, Jr.

[57] ABSTRACT

There is disclosed a process for the preparation of 1,3-diketones of formula I

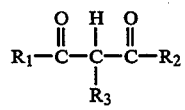

(I)

wherein $R_1$ and $R_2$ are each independently of the other $C_1$–$C_{20}$alkyl, phenyl or phenyl which is substituted by halogen, hydroxy, $NO_2$, $C_1$–$C_4$alkyl and/or $C_1$–$C_4$alkoxy, $C_7$–$C_9$phenylalkyl or a radical of formula II $$-A-X-R_4 \qquad (II)$$

wherein

A is $C_1$–$C_{12}$alkylene, phenylene or phenylene which is substituted by halogen, hydroxy, $NO_2$, $C_1$–$C_4$alkyl and/or $C_1$–$C_4$alkoxy, or is $C_1$–$C_{12}$alkylene which is substituted by hydroxy, halogen and/or alkoxy, X is oxygen or sulfur, and $R_4$ is hydrogen, $C_1$–$C_{18}$alkyl, phenyl or phenyl which is substituted by halogen, hydroxy, $C_1$–$C_4$alkyl, $NO_2$ and/or $C_1$–$C_4$alkoxy, or is $C_7$–$C_9$phenylalkyl, and $R_3$ is hydrogen, $C_1$–$C_{20}$alkyl, phenyl or phenyl which is substituted by halogen, hydroxy, $C_1$–$C_4$alkyl, $NO_2$ and/or $C_1$–$C_4$alkoxy, or is $C_7$–$C_9$phenylalkyl.

The process comprises carrying out a Claisen condensation of a ketone of formula III

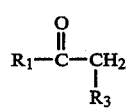

(III)

and an ester of formula IV (Abstract continued on next page.)

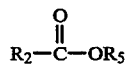 (IV)

or

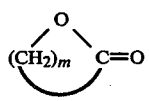 (V)

wherein $R_5$ is $C_1$–$C_5$alkyl, phenyl or phenyl which is substituted by halogen, $C_1$–$C_4$alkyl or hydroxy, the reaction being carried out with the base used as catalyst, a hydride of an alkali metal or alkaline earth metal or an alcoholate of $C_1$–$C_5$alkali metal or $C_1$–$C_5$alkaline earth metal, in a mixture of dimethyl sulfoxide and at least one organic solvent which is inert under the reaction conditions.

9 Claims, No Drawings

PROCESS FOR THE PREPARATION OF LINEAR 1,3-DIKETONES

This application is a continuation of application Ser. No. 07/860,297, filed Mar. 27, 1992, now abandoned.

This application is a continuation of application Ser. No. 690,021, filed Apr. 23, 1991 now abandoned.

The present invention relates to a process for the preparation of linear 1,3-diketones by a Claisen condensation of ketones with esters, in the presence of a hydride or alcoholate of an alkali metal or alkaline earth metal, and in a mixture of dimethyl sulfoxide and at least one organic solvent which is inert under the reaction conditions.

1,3-Diketones are disclosed in the literature as useful co-stabilisers for chlorinated polymers, especially polyvinyl chloride, which need to be protected against the harmful effects of heat and/or light. In addition, 1,3-diketones are important starting materials and intermediates for the synthesis of heterocycles. The Claisen condensation is commonly known in the an as a method of preparing 1,3-diketones and is described in numerous textbooks of organic chemistry, for example in Organikum, VEB Deutscher Verlag der Wissenschaften, Berlin (1969), pp. 580, 632, 658, J. B. Hendrickson, D. J. Cram, G. S. Hammond, Organic Chemistry, McGraw-Hill S. 522, 524, 525 or J. March, Advanced Organic Chemistry, J. Wiley & Sons (1985), pp. 437–39, 835.

The reaction for the preparation of diketones is normally carried out in an inert organic solvent in the presence of an alkali metal alcoholate as base. Thus, for example, the preparation of unsaturated $\beta$-diketones with an alkali metal alcoholate in diethyl ether is taught in U.S. Pat. No. 3,004,932. Other publications disclose the use of alkali metal hydrides as bases for the Claisen condensation. For example, in J. P. Anselme, Org. Synth. Vol 32 (1967), 3716, dibenzoylmethane is prepared by a Claisen condensation using sodium hydride as base in dimethyl sulfoxide.

Cyclic $\beta$-diketones are prepared in DE-A 1 618 442 by a Claisen condensation with an alkali metal alcoholate in an at least equimolar amount of dimethyl sulfoxide and, if desired, a further inert organic solvent.

As large excesses of ketones and lengthy reaction times are necessary to obtain good yields in the known Claisen condensation reactions, interest exists in providing improved processes for carrying out this reaction. Moreover, the method employed hitherto of isolating and purifying the synthesised diketones is complicated and troublesome. The provision of a simplified process would therefore be industrially useful.

Surprisingly, it has now been found that the reaction proceeds especially well by using a mixture of dimethyl sulfoxide and a further organic solvent which is inert under the reaction conditions. The reaction time is shortened and a very high yield is obtained.

Specifically, the invention relates to a process for the preparation of linear 1,3-diketones of general formula I $$R_1-\overset{O}{\underset{\|}{C}}-\overset{H}{\underset{|}{\underset{R_3}{C}}}-\overset{O}{\underset{\|}{C}}-R_2 \qquad (I)$$

wherein $R_1$ and $R_2$ are each independently of the other $C_1$-$C_{20}$alkyl, phenyl or phenyl which is substituted by halogen, hydroxy, $NO_2$, $C_1$-$C_4$alkyl and/or $C_1$-$C_4$alkoxy, or are $C_7$-$C_9$phenylalkyl or a radical of formula II $$-A-X-R_4 \qquad (II)$$

wherein

A is $C_1$-$C_{12}$alkylene, phenylene or phenylene which is substituted by halogen, hydroxy, $NO_2$, $C_1$-$C_4$alkyl and/or $C_1$-$C_4$alkoxy, or is $C_1$-$C_{12}$alkylene which is substituted by hydroxy, halogen and/or alkoxy, X is oxygen or sulfur, and $R_4$ is hydrogen, $C_1$-$C_{18}$alkyl, phenyl or phenyl which is substituted by halogen, hydroxy, $C_1$-$C_4$alkyl, $NO_2$ and/or $C_1$-$C_4$alkoxy, or is $C_7$-$C_9$phenylalkyl, and $R_3$ is hydrogen, $C_1$-$C_{20}$alkyl, phenyl or phenyl which is substituted by halogen, hydroxy, $C_1$-$C_4$alkyl, $NO_2$ and/or $C_1$-$C_4$alkoxy, or is $C_7$-$C_9$phenylalkyl, by a Claisen condensation of ketones of formula III $$R_1-\overset{O}{\underset{\|}{C}}-\overset{CH_2}{\underset{|}{\underset{R_3}{}}} \qquad (III)$$

with esters of formula IV $$R_2-\overset{O}{\underset{\|}{C}}-OR_5 \qquad (IV)$$

wherein $R_5$ is $C_1$-$C_5$alkyl, phenyl or phenyl which is substituted by halogen, $C_1$-$C_4$alkyl or hydroxy; or, if $R_2$ in formula I is $-(CH_2)_mOH$, also with cyclic esters of formula V $$\underset{(CH_2)_m}{\overset{O}{\diagup \diagdown}}\,C=O \qquad (V)$$

in which m is 2 to 10, in the presence of a hydride of an alkali metal or alkaline earth metal or of a $C_1$-$C_5$alcoholate of an alkali metal or alkaline earth metal as base, which process comprises carrying out the reaction in a mixture of dimethyl sulfoxide and at least one organic solvent which is inert under the reaction conditions.

$R_1$ and $R_2$ as $C_1$-$C_{20}$alkyl may be linear or branched and are typically methyl, ethyl, n-propyl, isopropyl, n-butyl, tert-butyl, n-pentyl, isopentyl, n-hexyl, n-heptyl, n-octyl, isooctyl, n-nonyl, decyl, undecyl, dodecyl, tridecyl, tetradecyl, pentadecyl, hexadecyl, heptadecyl, octadecyl, nonadecyl or eicosyl, preferably $C_1$-$C_{18}$alkyl, the most preferred meanings being methyl, isopentyl, n-nonyl, pentadecyl or heptadecyl.

$R_1$ or $R_2$ as substituted phenyl contains 1 to 3, preferably 1 or 2 substituents, preferably one substituent.

$R_1$ and $R_2$ as ($C_1$-$C_4$alkyl)phenyl may be phenyl which is substituted by 1 to 3, preferably by 1 or 2, alkyl groups, most preferably by methyl groups. Typical examples are tolyl, xylyl or mesityl.

$R_1$ and $R_2$ as halogen-substituted phenyl may be a phenyl ring which is substituted by one or more identical or different members selected from the group consisting of fluoro, chloro and bromo, preferably chloro or bromo, and are typically chlorophenyl or dichlorophenyl.

$C_1$-$C_4$Alkoxy is typically methoxy, ethoxy, propoxy or butoxy, and a correspondingly substituted phenyl group is typically methoxyphenyl.

$R_1$ and $R_2$ as $C_7$-$C_9$phenylalkyl may be benzyl, phenylethyl, α-methylbenzyl, 3-phenylpropyl or α,α-dimethylbenzyl. Benzyl is preferred. $R_1$ and $R_2$ are preferably $C_1$-$C_{18}$alkyl, phenyl, ($C_1$-$C_4$alkyl)phenyl or —A—X—$R_4$.

A as $C_1$-$C_{12}$alkylene may by linear or branched, preferably linear, alkylene. Typical examples of such radicals may be formed by adding the suffix -ene to the radicals cited above as suitable for $R_1$ and $R_2$ as alkyl up to the corresponding number of carbon atoms. $C_1$-$C_6$Alkylene is preferred, and n-propylene or n-pentylene are most preferred.

$R_4$ as $C_1$-$C_{18}$alkyl may be linear or branched alkyl as exemplified above in connection with $R_1$ and $R_2$ up to the corresponding number of carbon atoms.

$R_4$ as substituted phenyl or $C_7$-$C_9$phenylalkyl may have the same meanings as given for $R_1$ and $R_2$.

$R_4$ is preferably hydrogen, $C_1$-$C_{18}$alkyl or phenyl.

A as unsubstituted or substituted phenylene is preferably o- or p-phenylene, most preferably unsubstituted phenylene.

$R_3$ as $C_1$-$C_{20}$alkyl, substituted phenyl or $C_7$-$C_9$phenylalkyl may have the same meanings it as given for $R_1$ and $R_2$, and is preferably $C_1$-$C_4$alkyl.

$R_3$ is preferably hydrogen or $C_1$-$C_4$alkyl, but is most preferably hydrogen.

$R_5$ as $C_1$-$C_5$alkyl may be methyl, ethyl, n-propyl, isopropyl, n-butyl, tert-butyl, n-pentyl or isopentyl. More particularly, $R_5$ is $C_1$-$C_4$alkyl and is most preferably methyl.

$R_5$ as ($C_1$-$C_4$alkyl)phenyl may have the same meanings as given for $R_1$ and $R_2$.

The alkali metal hydride used is typically lithium hydride, sodium hydride or potassium hydride, more particularly sodium hydride or potassium hydride. Sodium hydride is most preferred.

Illustrative examples of alkaline earth metal hydrides are magnesium hydride and calcium hydride. Alkali metal hydrides are preferred.

Typical examples of $C_1$-$C_5$alkali metal alcoholates are $LiOCH_3$, $NaOCH_3$, $KOCH_3$, $LiOC_2H_5$, $NaOC_2H_5$, $KOC_2H_5$, $LiOn$—$C_3H_7$, $NaOn$—$C_3H_7$, $KOn$—$C_3H_7$ $LiOi$—$C_3H_7$, $NaOi$—$C_3H_7$, $KOi$—$C_3H_7$, $LiOn$—$C_4H_9$, $NaOn$—$C_4H_9$, $KOn$—$C_4$—$H_9$, $LiOi$—$C_4H_9$, $NaOi$—$C_4H_9$, $KOi$—$C_4H_9$, $LiOtert$—$C_4H_9$, $NaOtert$—$C_4H_9$, $KOtert$—$C_4H_9$, $LiOn$—$C_5H_{11}$, $NaOn$—$C_5H_{11}$, $KOn$—$C_5H_{11}$, $LiOi$—$C_5H_{11}$, $NaOi$—$C_5H_{11}$, $KOi$—$C_5H_{11}$, $LiOtert$—$C_5H_{11}$, $NaOtert$—$C_5H_{11}$, and $KOtert$—$C_5H_{11}$.

Typical examples of corresponding alkaline earth metal alcoholates are $Mg(OCH_3)_2$, $Ca(OCH_3)_2$, $Mg(OC_2H_5)_2$, $Ca(OC_2H_5)_2$, $Mg(On$—$C_3H_7)_2$, $Ca(On$—$C_3H_7)_2$, $Mg(Oi$—$C_3H_{72})$, $Ca(Oi$—$C_3H_7)_2$, $Mg(On$—$C_4H_9)_2$, $Ca(On$—$C_4H_9)_2$, $Mg(Otert$—$C_4H_9)_2$, $Ca(Otert$—$C_4H_9)_2$, $Mg(Oi$—$C_4H_9)_2$, $Ca(Oi$—$C_4H_9)_2$, $Mg(On$—$C_5H_{11})_2$, $Ca(On$—$C_5H_{11})_2$, $Mg(Oi$—$C_5H_{11})_2$, $Ca(Oi$—$C_5H_{11})_2$, $Mg(Otert$—$C_5H_{11})_2$, $Ca(Otert$—$C_5H_{11})_2$. Magnesium alcoholates are preferred.

It is preferred to use alkali metal alcoholates, more particularly sodium alcoholates such as $NaOCH_3$, $NaOC_2H_5$ and $NaOtert$—$C_4H_9$, most preferably $NaOCH_3$ and $NaOtert$-$C_4H_9$.

Organic solvents which are inert under the reaction conditions are typically linear or cyclic ethers, aliphatic or aromatic hydrocarbons, or cyclic or linear amides.

Linear or cyclic ethers may be mono-, di-, tri- or polyethers.

Illustrative examples of such ethers are: diethyl ether, diisopropyl ether, methyl tert-butyl ether, dibutyl ether, ethylene glycol dimethyl ether, diethylene glycol dimethyl ether, tetrahydrofuran, tetrahydropyran, dioxane or dioxolane. Cyclic ethers and higher linear ethers (for example those containing from 5 carbon atoms) are preferred, preferably dioxane, diethylene glycol dimethyl ether, tetrahydrofuran or methyl tert-butyl ether. Mixtures of these solvents may also be used.

Aliphatic hydrocarbons which may be suitably be used are pentane, hexane, heptane, octane, cyclohexane, decalin, petroleum ether or mixtures thereof. Aromatic hydrocarbons which are conveniently used are typically benzene, toluene or xylene. Toluene is preferred.

A suitable cyclic or linear amide is N-methyl-pyrrolidone.

Preferred inert organic solvents are dioxane, tetrahydrofuran, diethylene glycol dimethyl ether, methyl tert-butyl ether, toluene or N-methylpyrrolidone.

Particular interest attaches to the preparation of compounds of formula I, wherein $R_1$ and $R_2$ are each independently of the other $C_1$-$C_{20}$alkyl, phenyl, ($C_1$-$C_4$alkyl)phenyl or a radical of formula II, A is $C_1$-$C_6$alkylene, $R_4$ is hydrogen, $C_1$-$C_{18}$alkyl, phenyl or ($C_1$-$C_4$alkyl)phenyl, and $R_3$ is hydrogen and $C_1$-$C_4$alkyl.

Preferred compounds of formula I are those wherein $R_1$ and $R_2$ are each independently of the other $C_1$-$C_8$alkyl, phenyl or a radical of formula II, $R_4$ is hydrogen, phenyl or $C_1$-$C_{18}$alkyl, and $R_3$ is hydrogen.

The key feature of the invention consists in the use, in the above described process, of a mixture of dimethyl sulfoxide and at least one organic solvent which is inert under the reaction conditions. It is preferred to use mixtures containing typically 10–80%, preferably 10–60% and, most preferably, 15–50%, of dimethyl sulfoxide. Mixtures containing 20–70%, typically 30–60%, of dimethyl sulfoxide are also useful.

Solvent mixtures which do not contain dimethyl formamide are preferred. The reaction mixture may also contain minor amounts of the alcohol corresponding to the respective alkali metal or alkaline earth metal alcoholate.

The process of this invention is conveniently carried out in the temperature range from −20° to +70° C., preferably from −5° to +40° C.

The reaction times of the above described Claisen condensation may vary within a wide range, but are normally from 0.5 to 5.0 hours.

The possibility of a simplified working up after the reaction is also important. This working up consists in isolating the alkali metal salt or alkaline earth metal salt of the diketone direct from the reaction solution, washing said salt, and subsequently obtaining the pure diketone after hydrolysis with a dilute acid. Suitable acids are typically acetic acid, formic acid, phosphoric acid, hydrochloric acid and sulfuric acid, preferably hydrochloric acid and sulfuric acid.

As mentioned at the outset, the linear 1,3-diketones obtainable by the process of this invention are useful co-stabilisers for chlorinated polymers which need to be protected against the harmful effect of heat and/or light. Consequently an interest exists in preparing these diketones in high yield by the simplest possible methods with a low energy consumption.

The process of this invention opens up an industrially particularly advantageous and economic route to the preparation of these compounds.

An important advantage of the process of this invention is that relatively low reaction temperatures are required for carrying it out. The resultant energy-saving is a major aspect of the industrial application of the process. The process can, the example, be carried out in the temperature range from −20° to +70° C., preferably from −5° to +40° C. An increase in the reaction temperature does not necessarily lead to an increase in yield. In the prior art processes, the use of an up to 100% excess of ketone is necessary to obtain good yields. A particular technical advantage of the process of the invention therefore also resides in the possibility afforded of reducing the excess of educt and base compared with the prior art processes, thereby diminishing the waste disposal problems. The process of the invention thus also makes it possible to obtain high yields using approximately stoichiometric amounts or small excesses of ester. The ester component and/or base are conveniently added in an amount of 0.5–1.5 tool, preferably 0.65–1.25 mol, most preferably 0.9–1.2 tool, based on 1 mol of ketone.

The reaction is advantageously carried out, for example, by charging the base in the solvent to the reactor and adding the ester and ketone components in succession or simultaneously. Conventional operations, such as stirring the reaction mixture, are useful. A preferred embodiment of the process of the invention also comprises a simplified means of working up the reaction product, which does not—as hitherto known—absolutely need to be hydrolysed in the reaction solution and then extracted with the aid of organic solvents, but is isolated from the reaction solution in the form of the precipitated alkali metal salt or alkaline earth metal salt (if necessary after removal of at least a portion of the solvent and, if desired, after addition of a solvent in which the salt is insoluble), washed, and the pure isolated salt is then hydrolysed. One advantage is that the organic solvent is not contaminated with water and can be readily reused.

In addition, this method of working up gives reaction products of high purity, as organic by-products can be removed together with the solvent, whereas these products, when working up by extraction, are extracted together with the desired reaction product and contaminate it.

As known to the skilled person, some or all of the compounds of formula I can naturally be obtained in the tautomeric forms according to the equilibrium

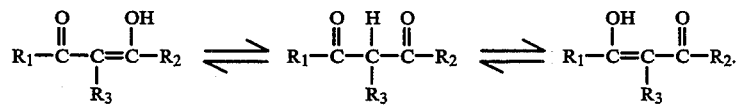

The invention is illustrated in more detail by the following Examples in which, as well as throughout the description and claims, parts and percentages are by weight, unless otherwise stated.

EXAMPLE 1

1,3-Diphenylpropane-1,3-Dione (Dibenzoylmethane)

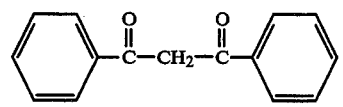

In a 0.5 l Sovirel flask (double-walled reactor) fitted with stirrer, thermometer, dropping funnel and reflux condenser with bubble counter, 100 g of anhydrous dimethyl sulfoxide (DMSO) and 100 g of tetrahydrofuran and 10 g of sodium hydride (80% in paraffin oil) are cooled to 5° C. and a mixture of 45 g of methyl benzoate and 36 g of acetophenone is added dropwise over 60 minutes at 5°–10° C. When the addition is complete, the mixture is stirred for 10 minutes at 5° C., then warmed to 30° C. and transferred to a 1 liter single-necked flask. The low boiling fractions are removed by distillation on a rotary evaporator, and the residue (203 g) is dissolved in 800 ml of ice-water. After acidification with 30 g of 50% sulfuric acid and stirring for 10 minutes, the precipitated crystals are filtered with suction, washed with water and dried to constant weight.

Yield: 63.6 g=94.5% of theory of pale yellow crystals with a melting point of 72°–75° C.

Purity of the dibenzoylmethane according to gas chromatography: 98.2%.

EXAMPLE 2

1,3-Diphenylpropane-1,3-Dione (Dibenzoylmethane)

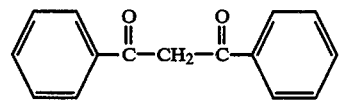

100 g of anhydrous dimethyl sulfoxide, 100 g of diethylene glycol dimethyl ether, 6 g of absolute methanol and 18 g of sodium methylate (97%) are charged to an apparatus as described in Example 1. A mixture of 45 g of methyl benzoate and 36 g of acetophenone are added dropwise to this mixture at 25 ° C. over 45 minutes. After this addition, the reaction mixture is stirred for 2 hours at 30° C. and the solvent is removed by vacuum distillation at a temperature of <60 ° C. The residue is diluted with 150 g of methyl tert-butyl ether, cooled to 0° C. and filtered. The filter cake is washed twice with methyl tert-butyl ether. The pale grey solid is thereafter taken up in dilute hydrochloric acid and stirred.

The product is isolated by filtration and dried to constant weight.

Yield: 61.3 g=91.1% of theory of white to pale yellow crystals with a melting point of 72°–75° C.

EXAMPLE 3

1-Phenylbutane-1,3-dione

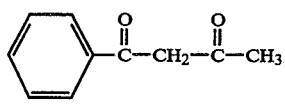

The procedure of Example 1 is repeated, using in place of acetophenone 17.4 g of acetone and increasing the amount of solvent from 100 g to 150 g of dimethyl sulfoxide/tetrahydrofuran.

Yield: 42.6 g ≙ 87.5% of theory of a yellow crystalline powder with a melting point of 52°–53° C.

The NMR spectrum confirms that a mixture of 14% of

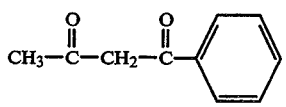

and 86% of

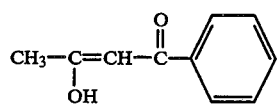

is obtained.

EXAMPLE 4

6-Methyl-1-Phenylheptane-1,3-Dione

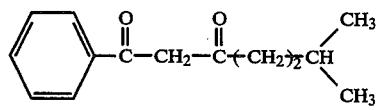

The procedure as described in Example 1 is repeated, replacing acetophenone with 34.5 g of 5-methyl-2-hexanone.

Working up after acidification of the reaction mixture with sulfuric acid is effected by extracting the aqueous solution with 2×100 ml of dichloromethane, then drying the extract over sodium sulfate, stripping off the solvent on a rotary evaporator and purifying the residue by distillation.

Yield: 52.8 g ≙ 80.6% of theory of a yellow fluid with a boiling point of 98°–100° C./0.2 mbar and a refractive index $n_D^{20}$:1.5505.

EXAMPLE 5

1-Phenyldodecane-1,3-Dione

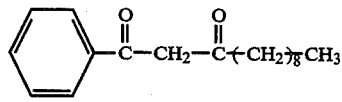

The procedure as described in Example 1 is repeated, replacing acetophenone with 51.0 g of 2-undecanone.

Working up is as described in Example 4.

Yield: 74.6 g ≙ 90.7% of theory of a colourless fluid with a boiling point of 140°–42° C./0.25 mbar and a melting point of 36°–37° C.

EXAMPLE 6

1-Phenyl-6-N-Dodecylthiohexane-1,3-Dione

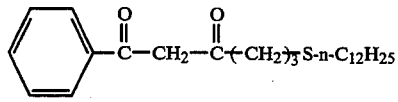

The procedure as described in Example 1 is repeated, but using 24 g of acetophenone and replacing methyl benzoate and sodium hydride with 66.6 g of methyl n-dodecylthiobutyrate and 21.2 g of sodium ten-butylate. Tetrahydrofuran is replaced by the same amount of toluene and the reaction temperature is 0° C.

Yield after recrystallisation from isopropanol/water: 55.7 g ≙ 71.4% of theory of white crystals with a melting point of 44° C.

EXAMPLE 7

1-Phenyl-6-Phenylthio-Hexan-1,3-dion

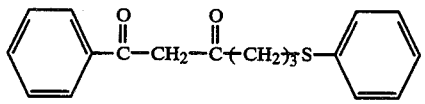

The procedure as described in Example 1 is repeated, using 18 g of acetophenone and 4.9 g of sodium hydride and replacing methyl benzoate with 34.7 g of methyl n-phenylthiobutyrate. Working up is effected as described in Example 4.

Yield: 33.4 g ≙ 74.4% of theory of a yellow fluid with a boiling point of 178°–82° C./0.13 mbar and a refractive index $n_D^{20}$ 1.6185.

EXAMPLE 8

8-Hydroxy-1-Phenyloctane-1,3-Dione

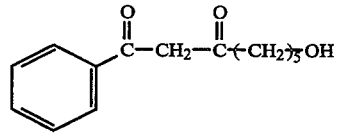

A 0.5 l Sovirel flask (double-walled reactor) fitted with stirrer, thermometer, separating funnel and distillation receiver is charged, under nitrogen, with 99.0 g of sodium methylate solution (30% solution in methanol) and 117 g of dimethyl sulfoxide. Ca. 62 g of methanol are distilled from this solution, and the resultant suspension is cooled. Then 100 g of N-methylpyrrolidone are added at 30° C. and the batch is cooled to 0° C. At this temperature, a solution of 60.0 g of acetophenone, 62.8 g of ε-caprolactone and 17.0 g of N-methylpyrrolidone are added over 1 hour. The mixture is stirred for 30 minutes at 0° C. and for 2 hours at 20° C. At a sump temperature of <70° C., ca. 120 g of solvent are distilled from the product solution. After cooling to 30° C., 300 ml of water are added to the residue. The solution is extracted with 3×70 ml of xylene, the aqueous phase is diluted with water to 1200 ml, and the pH is then adjusted to 5.5 with ca. 28 ml of 50% sulfuric acid. The precipitated product is isolated by filtration, washed on the filter with 100 ml of water and dried to constant weight under vacuum at ca. 30° C.

Yield: 85.0 g≙72.6% of theory of slightly yellowish crystals with a melting point of 46°–48° C.

Purity according to gas chromatography: 97.3%.

EXAMPLE 9

6-Hydroxy-1-Phenylhexane-1,3-Dione

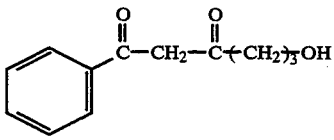

60.0 g of acetophenone, 47.4 g of butyrolactone and 99.0 g of sodium methylate (30% solution in methanol) are reacted in the same manner as described in Example 8. After working up as described in Example 8, the product precipitates from the mother solution after several hours. The precipitate is isolated by filtration, washed with water and dried to constant weight under vacuum at ca. 30° C.

Yield: 70.0 g≙68% of theory of yellow crystals with a melting point of 35° C.

EXAMPLE 10

8-Hydroxy-1-Phenyloctane-1,3-Dione

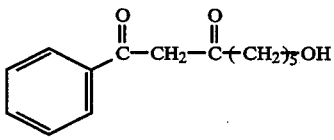

An apparatus as described in Example 8 is charged with 30.8 g of sodium methylate (97%), 117.0 g of DMSO and 117.0 g of dioxane and the mixture is cooled to 0° C. At this temperature, a solution of 61.3 g of acetophenone, 57.7 g of ε-caprolactone and 17.0 g of dioxane are added, with stirring, over 1 hour. Stirring is continued for 30 minutes at 0° C. and then for 2 hours at 20° C. Subsequently ca. 220 g of solvent are distilled from the reaction mixture at 70° C. and under reduced pressure.

300 g of water are added to the residue and the suspension is extracted with 3×70 ml of xylene. The aqueous phase is diluted to 1000 ml and adjusted to pH ~5 with sulfuric acid. The precipitated product is isolated by filtration and dried.

Yield: 78.1 g≙66.6% of theory of yellowish crystals with a melting point of 47°–50° C.

Replacing the sodium methylate with 52.9 g of sodium tert-butylate gives a yield of 79.0 g=67.4% of theory.

EXAMPLE 11

8-Hydroxy-1-Phenyloctane-1,3-Dione

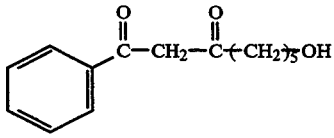

In accordance with the procedure of Example 8, 61.3 g of acetophenone and 57.7 g of ε-caprolactone are condensed in 117.0 g of N-methylpyrrolidone as solvent with 52.9 g of sodium tert-butylate (97%) as base. Working up is as described in Example 8.

Yield: 73.0 g≙62.3% of theory of yellowish crystals with a melting point of 47°–50° C.

EXAMPLE 12

1,3-Diphenyl-Propan-1,3-Dion

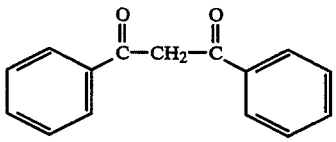

An apparatus as described in Example 1 is charged with 18.0 g of sodium methylate (97%), 100 g of DMSO, 100 g of dioxane and 6 g of methanol and the mixture is cooled to 0° C. Then a mixture of 45 g of methyl benzoate and 36 g of acetophenone are added dropwise over 35 minutes. The reaction mixture is then stirred for ca. 45–60 minutes at 30° C.

WORKING UP METHOD A

The solvent is distilled off on the rotary evaporator (bath temperature <60° C.) and the residue is dissolved in 800 ml of water. The aqueous solution is acidified with dilute hydrochloric acid and the precipitate is isolated by filtration, washed with water and dried.

Yield: 60.0 g≙89.2% of theory.

Purity: >98% determined by $^{13}$C-NMR spectroscopy.

Melting point: 72°–75° C.

WORKING UP METHOD B

The solvent is removed by distillation in the Sovirel reactor (bath temperature <60° C.) so long as the residue can be stirred. The oily residue is then taken up in 200 ml of methyl tert-butyl ether (MTBE), and the ethereal solution is cooled to 0° C. and filtered. The filter residue is washed with 2×100 ml of NITBE and with 2×50 ml of petroleum ether (50°–70° C). The pale grey solid is taken up in 500 ml of water, the aqueous solution is acidified with dilute hydrochloric acid, and the precipitate is isolated by filtration and dried.

Yield: 58.1 g≙86.3% of theory.

Purity: >98% determined by $^{13}$C-NMR spectroscopy.

Melting point: 72°–75° C.

EXAMPLE 13

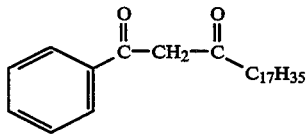

99 g of methyl stearate and 36 g of acetophenone are condensed in accordance with the procedure described in Example 12.

WORKING UP METHOD A

The solvent is removed by distillation on the rotary evaporator (bath temperature <60° C.) and the residue is taken up in 1000 ml of water. The aqueous solution is acidified with dilute hydrochloric acid and the precipitate is isolated by filtration, washed with 350 ml of methanol and dried (109.1 g=94% of theory). The crude product is crystallised by fractional crystallisation from 600 ml of boiling methanol.

Yield: 78.8 g=68% of theory.

Purity: >98% determined by $^{13}$C—NMR spectroscopy.

Melting point: 60°–64° C.

WORKING UP METHOD B

The solvent is removed by distillation in the Sovirel reactor (bath temperature <60° C.) so long as the residue can be stirred. The oily residue is then taken up in 200 ml of methanol and the methanolic solution is cooled to 20° C. and filtered. The filter residue is washed with 2×100 ml of methanol. The pale grey solid (sodium salt of the diketone) is taken up in 750 ml of water and the aqueous solution is acidified with dilute hydrochloric acid, and the precipitate is isolated by filtration and dried.

Yield: 87.6 g≐75.5% of theory.

Melting point: 60°–64° C.

EXAMPLE 14

1-Phenyloctadecane-1,3-Dione

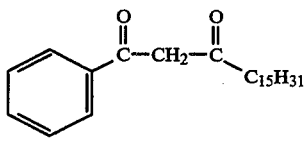

An apparatus as described in Example 1 is charged with 31.7 g of sodium-tert-butylate, 150 g of DMSO and 150 g of tetrahydrofuran (THF) and the mixture is cooled to 0° C. Then a mixture of 89 g of methyl palmitate and 36 g of acetophenone is added dropwise over 45 minutes. The reaction mixture is then stirred for ca. 45–60 minutes at 30° C., the solvent is removed by distillation on a rotary evaporator (bath temperature <60° C.), and the residue is taken up in 1000 ml of water. The aqueous solution is acidified with dilute hydrochloric acid and the precipitate is isolated by filtration, washed with water, and dried.

The crude product (110.6 g) is crystallised once by fractional crystallisation from 400 ml of methanol.

Yield: 68.9 g≐64.0% of theory.

Purity: >98% determined by $^{13}$C—NMR spectroscopy.

Melting point: 62°–65° C.

EXAMPLE 15

1,4-Diphenylbutane-1,3-Dione

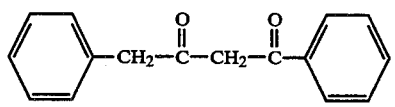

The procedure as described in Example 1 is repeated, using in place of sodium hydride 31.7 g of sodium tert-butylate and, in place of methyl benzoate, 54.2 g of ethyl phenylacetate.

Yield: 60.7 g≐84.9% of theory of a yellow waxlike substance, which is recrystallised from 200 ml of isopropanol/30 ml of water. Melting point 47°–48° C.

EXAMPLE 16

Temperature Profile of the Process

All reactions are carried out for dibenzoylmethane (product of Example 1) in dimethyl sulfoxide/dioxane with sodium methylate as base +3% methanol. The process described in Example 1 is carried out. The reaction temperature is varied from 0° to 70° C.

The results are reported in Table 1.

TABLE 1

| Reaction temperature in °C. | Yield in % | Purity in % |
|---|---|---|
| 0 | 89.2 | 99 |
| 10 | 91.4 | 97 |
| 20 | 90.3 | 98 |
| 30 | 90.3 | 94 |
| 50 | 80.8 | 99 |
| 70 | 82.4 | 96 |

The experiments show that an increase in temperature above 50° C. results in no further increase in yield.

What is claimed is:

1. A process for the preparation of a linear 1,3-diketone of formula I

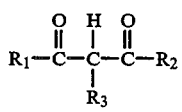

wherein

R$_1$ and R$_2$ are each independently of the other C$_1$–C$_{20}$alkyl, phenyl or phenyl which is substituted by halogen, hydroxy, NO$_2$, C$_1$–C$_4$alkyl and/or C$_1$–C$_4$alkoxy, or are C$_7$–C$_9$phenylalkyl or a radical of formula II $$—A—X—R_4 \qquad (II)$$

wherein

A is C$_1$–C$_{12}$alkylene, phenylene or phenylene which is substituted by halogen, hydroxy, NO$_2$, C$_1$–C$_4$alkyl and/or C$_1$–C$_4$alkoxy, or is C$_1$–C$_{12}$alkylene which is substituted by hydroxy, halogen and/or alkoxy, X is oxygen or sulfur, and R$_4$ is hydrogen, C$_1$–C$_{18}$alkyl, phenyl or phenyl which is substituted by halogen, hydroxy, C$_1$–C$_4$alkyl, NO$_2$ and/or C$_1$–C$_4$alkoxy, or is C$_7$–C$_9$phenylalkyl, and R$_3$ is hydrogen, C$_1$–C$_{20}$alkyl, phenyl or phenyl which is substituted by halogen, hydroxy, C$_1$–C$_4$alkyl, NO$_2$ and/or C$_1$–C$_4$alkoxy, or is C$_7$–C$_9$phenylalkyl, by a Claisen condensation of a ketone of formula III

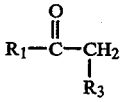

with an ester of formula IV

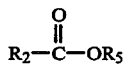

wherein $R_5$ is $C_1$–$C_5$alkyl, phenyl or phenyl which is substituted by halogen, $C_1$–$C_4$alkyl or hydroxy; or, when $R_2$ in formula I is —$(CH_2)_m OH$, also with a cyclic ester of formula V

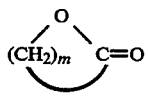

in which m is 2 to 10, in the presence of a $C_1$–$C_5$alcoholate of an alkali metal or alkaline earth metal as base, which process comprises
carrying out the reaction in a mixture of dimethyl sulfoxide and at least one organic solvent which is inert under the reaction conditions which inert solvent is selected from the group consisting of dioxane, tetrahydrofuran, diethylene glycol dimethyl ether, methyl tert-butyl ether, toluene and N-methylpyrrolidone and in which process the Claisen condensation reaction is carried out in the temperature range from −20° to +70° C.

2. A process according to claim 1 for the preparation of a compound of formula I, wherein
$R_1$ and $R_2$ are each independently of the other $C_1$–$C_{20}$alkyl, phenyl, ($C_1$–$C_4$)phenyl or a radical of formula II,
A is $C_1$–$C_6$alkylene,
$R_4$ is hydrogen, $C_1$–$C_{18}$alkyl, phenyl or ($C_1$–$C_4$alkyl)phenyl, and
$R_3$ is hydrogen $C_1$–$C_4$alkyl.

3. A process according to claim 2 for the preparation of a compound of formula I, wherein
$R_1$ and $R_2$ are each independently of the other $C_1$–$C_{18}$alkyl, phenyl or a radical of formula II,
$R_4$ is hydrogen, phenyl or $C_1$–$C_{18}$alkyl, and
$R_3$ is hydrogen.

4. A process according to claim 1, wherein the amount of dimethyl sulfoxide in the mixture with at least one organic solvent which is inert under the reaction conditions is 10 to 80%.

5. A process according to claim 1, wherein the reaction is carried out in the temperature range from −5° to +40° C.

6. A process according to claim 1, wherein the reaction time of the Claisen condensation is from 0.5 to 5 hours.

7. A process according to claim 1, wherein the alkali metal salt or alkaline earth metal salt of the diketone is precipitated direct from the reaction solution and isolated, and the diketone is obtained pure by hydrolysis with dilute acid.

8. A process according to claim 1, wherein the base is a sodium alcoholate.

9. A process according to claim 1, wherein the base is $NaOCH_3$ or $NaO$-$t$-$C_4H_9$.

* * * * *